United States Patent [19]

Collins et al.

[11] Patent Number: 5,354,550
[45] Date of Patent: * Oct. 11, 1994

[54] VISUALLY CLEAR GEL DENTIFRICE

[75] Inventors: Michael A. Collins, Keyport; Joan M. Duckenfield, North Brunswick, both of N.J.

[73] Assignee: Colgate Palmolive Company, New York, N.Y.

[ * ] Notice: The portion of the term of this patent subsequent to Jul. 16, 2008 has been disclaimed.

[21] Appl. No.: 44,690

[22] Filed: Apr. 12, 1993

Related U.S. Application Data

[63] Continuation of Ser. No. 812,511, Dec. 20, 1991, Pat. No. 5,253,313.

[51] Int. Cl.⁵ ............................ A61K 7/16; A61K 7/18
[52] U.S. Cl. ......................................... 424/49; 424/52; 424/57
[58] Field of Search ........................................ 427/49–58

[56] References Cited

U.S. PATENT DOCUMENTS

| Number | Date | Name | Class |
|---|---|---|---|
| 4,036,949 | 7/1977 | Colodney | 424/49 |
| 4,069,310 | 1/1978 | Harrison | 424/49 |
| 4,108,978 | 8/1978 | Mazzanobile et al. | 424/49 |
| 4,238,476 | 12/1980 | Harvey | 424/52 |
| 4,435,380 | 3/1984 | Pader | 424/49 |
| 5,013,541 | 5/1991 | Elliott et al. | 424/52 |
| 5,015,467 | 5/1991 | Smitherman | 424/52 |
| 5,096,701 | 3/1992 | White et al. | 424/52 |
| 5,145,667 | 9/1992 | Ibrahim et al. | 424/52 |
| 5,176,900 | 1/1993 | White et al. | 424/52 |
| 5,188,821 | 2/1993 | Gaffar et al. | 424/52 |
| 5,192,529 | 3/1993 | Garlick et al. | 424/49 |

FOREIGN PATENT DOCUMENTS

| 0333301 | 9/1989 | European Pat. Off. . |
| 0354447 | 2/1990 | European Pat. Off. . |
| 1407787 | 9/1975 | United Kingdom . |

*Primary Examiner*—Shep K. Rose
*Attorney, Agent, or Firm*—Robert L. Stone; Murray M. Grill

[57] ABSTRACT

A visually clear gel dentifrice comprising a polishing agent having a refractive index of about 1.41 to 1.47, a water-swellable synthetic anionic polycarboxylate polymer and a liquid vehicle of about 25–30% by weight water and 30–45% by weight of neat humectant wherein at least about 30% by weight of said dentifrice is neat sorbitol.

14 Claims, No Drawings

VISUALLY CLEAR GEL DENTIFRICE

This is a continuation of application Ser. No. 812,511 filed Dec. 20, 1991, now U.S. Pat. No. 5,252,313 issued Oct. 12, 1993.

This invention relates to an antiplaque gel dentifrice which is visually clear.

Dentifrices which are visually clear are appealing to consumers. Numerous visually clear products have been sold commercially as gel dentifrices.

Occasionally, as described in U.S. Pat. No. 3,906,090 to Colodney, it is possible to attain very high clarity and transparency in a gel dentifrice. Frequently, however, because of the need to appropriately balance amounts and types of dentifrices components for optimum effectiveness and for cosmetic considerations other than translucency, clarity is sacrificed and the gel dentifrice, while still clear, is translucent, hazy or cloudy and not transparent. Indeed, the gel dentifrice may be opacified and not clear at all.

The prior art considerations for attaining clarity ranging from haze or translucency to nigh transparency have, in general, been based upon employing a dentifrice polishing agent having a refractive index of about 1.41 to about 1.47, properly balanced with water (refractive index 1.333) and humectant, most usually glycerin (refractive index 1.473 ) and sorbitol (refractive index 1.457, as 70% aqueous solution). Since the refractive index of grades of siliceous polishing agents, the most frequently used type of polishing agents in gel dentifrices, is usually about 1.41 to about 1.47, although water ranges in the dentifrices such as up to about 30% by weight have been disclosed, the amount of water is generally kept low, say about 3% by weight, when transparency and not merely turbid translucency is desired.

An exception permitting more water to be used in transparent gel dentifrices is described in U.S. Pat. No. 4,877,602 to Uematsu et al, wherein a special grade of sodium carboxymethyl cellulose binding agent having a viscosity of 5-20 cps measured as 1% aqueous solution at 25° C. is indicated to provide transparency to gel dentifrices wherein the liquid vehicle components vary over a wide range.

In more recent years, water-swellable synthetic anionic polymeric polycarboxylates have been introduced into oral compositions, particularly as agents which improve effectiveness in combatting negative conditions such as tartar and plaque. In antiplaque dentifrices, there is desirably present a substantially water-insoluble noncationic antibacterial agent such as triclosan (2,4,6'-trichloro-2-hydroxy-diphenyl ether). Such polycarboxylates are disclosed in British Patent Publications 2235133A, 2227660A and 2200551A, each to Colgate-Palmolive Company and U.S. Pat. No. 4,894,220 to Nabi et al, the disclosures of each of which are incorporated herein by reference. These disclosures set forth guides to preparing visually clear antiplaque dentifrices wherein there are described gel dentifrices containing about a siliceous polishing agent; broad weight ranges of water and humectant are indicated. This general guidance and specific illustrative examples within their parameters have provided some visual translucency but have not led to high transparency.

In antitartar dentifrices such as in U.S. Pat. No. 4,627,977 to Gaffar et al the disclosure of which is incorporated herein by reference, and in antiplaque dentifrices such as those of incorporated aforementioned British Patent Publications 2235133A; 2227660A; 2200551A and U.S. Pat. No. 4,894,220, the polymeric materials have been described as present in a range of amounts such as up to about 3% or 4% by weight.

In practice, it has been observed that high visual clarity has been difficult to attain when the amount of polymer is at least about 1% by weight, and particularly when it is present in amount of about 2% by weight or more.

It is an advantage of this invention that excellent visual clarity is attained in a dentifrice containing water-swellable synthetic anionic polymer in amount of about 1%-4% with a particular liquid vehicle. It is noteworthy that liquid vehicles in dentifrices containing the polymer have not been particularly successful in providing gel dentifrice with superior visual clarity. Indeed, even liquid vehicles disclosed in U.S. Pat. No. 4,277,602 have not been employed in conjunction with water-swellable polymers which markedly affect the liquid vehicle.

Other advantages of the invention will be apparent from consideration of the following specification.

In accordance with certain of its aspects, this invention relates to a visually clear gel dentifrice comprising about 5-50% by weight of a dentally acceptable dentifrice polishing agent having a refractive index in the range of about 1.41 to about 1.47, about 0.1-10% by weight of a gelling agent to provide a gel consistency to said dentifrice, a liquid vehicle comprising an amount of about 25%-30% by weight of said dentifrice of total water and about 30-45% by weight of said dentifrice on a neat basis of humectant material wherein sorbitol is present in neat amount of at least about 30% by weight of said dentifrice and about 1%-4% neat amount by weight of dentifrice of a water-swellable synthetic anionic polycarboxylate polymer.

The dentally acceptable dentifrice polishing agent has a refractive index in the range of about 1.41 to about 1.47. Thus, it may be a finely divided synthetic amorphous silica having an average refractive index of from about 1.410 to 1.440 as has been described for translucent dental creams in U.S. Pat. Nos. 3,939,262 and 4,007,260, each to Kim or an alkali metal phosphate salt having a refractive index between 1.435 and about 1.465 as has been described in U.S. Pat. No. 3,927,202 to Harvey et al. The alkali metal phosphate polishing agents described therein are potassium metaphosphate, which is water-insoluble and water-soluble sodium pyrophosphate dodecahydrate, dibasic sodium orthophosphate dihydrate, dibasic sodium orthophosphate heptahydrate, dibasic sodium orthophosphate dodecahydrate and tribasic sodium orthophosphate dodecahydrate.

Preferably the polishing agent is a siliceous material such as a hydrous silica gel, a silica xerogel or a complex amorphous alkali metal aluminosilicate or zirconosilicate having a refractive index of about 1.44 to 1.48 or a precipitated silica having a refractive index of about 1.41 to 1.45. Colloidal silica materials include those sold under the trademark SYLOID such as those which have been sold as Syloid 72 and Syloid 74. Precipitated silicas include those sold under the trademark ZEODENT such as Zeodent 113 and Zeodent 115 and Zeodent 119.

The complex aluminosilicate salt appears to contain interbonded silica and alumina having Al-O-Si bonds as described by Tamele, "Chemistry of the Surface and Activity of Alumina-Silica Cracking Catalyst", Discussions of the Faraday Society, No. 8 Pages 270–279 (1950) and particularly at Page 273, FIG. 1, Curve 3 wherein the interaction between silica and aluminum ions is potentiometrically detected. Further literature describing this type of complex includes Milliken et al., "The Chemical Characteristics and Structure of Cracking Catalysts", Discussions of the Faraday Society, No. 8, Pages 279–290 (1950) and particularly the sentence bridging Pages 284–285. These complexes clearly differ from silica gel as is described by Plank et al., "Differences Between Silica and Silica-Alumina Gels I. Factors Affecting the Porous Structure of These Gels," Journal of Colloid Science, 2. Pages 399–412 (1947) and Plank, "Differences Between Silica and Silica-Alumina Gels II. A Proposed Mechanism for the Gelation and Syneresis of These Gels." Journal of Colloid Science 2, Pages 413–427, (1947) in which formation of the Al-O-Si bond is described at Pages 419–422.

The polishing agent is present in amount of about 5–50% by weight, preferably about 10–30% and most preferably about 15–25%.

Water has a refractive index of 1.333. Since this is substantially lower than the refractive index of the polishing agent, low amounts of water, for instance about 3% by weight, usually have been employed when high visual clarity is desired. However, since the water swellable synthetic anionic polymeric polycarboxylate is swelled and hydrated by water and moreover when the polymer is present in amount of at least 1% by weight, substantial amounts of water have been used in such formulations. Indeed, in such formulations, 35% of water has been employed to hydrate about 1%–2% by weight of polymer solid. In such formulations, when polishing agent of refractive index of about 1.41 to 1.47 has been employed, a highly visually clear gel containing about 1%–4% of the polymer has not previously been attained.

In the present invention it has been found that a particular balance of liquid vehicle components, specifically water and sorbitol, permits the polymer to be satisfactorily hydrated while still providing a refractive index of the liquid vehicle such that the gel dentifrice is highly transparent.

The liquid vehicle of the dentifrice comprises about 25%–30% by weight of total water and about 30–45% by weight of neat humectant. Sorbitol is the main or only humectant component. It is commercially available in 70% aqueous solution (refractive Index 1.457) and is employed in amount such that as the 70% aqueous solution it is present in amount by weight corresponding to about 43%–65%, corresponding to about 30%–45% by weight of neat sorbitol, the remainder aqueous solvent being part of the total water. Other humectants may be present in amount up to 15% by weight on a neat basis preferably about 3–10%. These include glycerine (typically available in 99.5% aqueous solution), propylene glycol, polypropylene glycol and polyethylene glycol. Glycerine (refractive index 1.473) is preferred. It is preferred not to use polyethylene glycol when substantially water-insoluble noncationic antibacterial agent, such as triclosan, is present.

Water-swellable synthetic anionic polymeric polycarboxylate having a molecular weight of about 1,000 to about 1,000,000, preferably about 30,000 to about 500,000, have been used in optimizing anticalculus effectiveness of linear molecularly dehydrated polyphosphate salts, as disclosed in incorporated U.S. Pat. No. 4,627,977 to Gaffar et al.

The water-swellable synthetic anionic polymeric polycarboxylates are preferably employed as partially or completely neutralized water swellable alkali metal (or ammonium) salts but may also be used as their free acids. Preferably they are 4:1 to 1:4 copolymers of maleic anhydride or maleic acid with another polymerizable ethylenically unsaturated monomer, which is very preferably methyl vinyl ether, and the copolymer will have a molecular weight in the range of about 5,000–2,000,000, preferably about 30,000–1,500,000, more preferably about 50,000–1,100,000 and most preferably about 50,000–100,000, as determined by vapor pressure osmometry. A preferred range of molecular weights, by gel permeation chromatography against a polyethylene glycol standard, is about 500,000–1,500,000, more preferably about 1,000,000–1,100,000, e.g., about 1,090,000. Useful such polycarboxylates include Luviform FA-139 of BASF and GAF's Gantrezes AN 169, AN 139, AN 119 and S-97, pharmaceutical grade. The Gantrez polycarboxylates have been reported by their manufacturer to be of molecular weights of about 750,000, 500,000, 250,000 and 70,000, respectively, but by gel permeation chromatography determinations (against a polyethylene glycol standard) the S-97, pharmaceutical grade, is of a molecular weight in the range of about 1,000,000–1,100,000 (the lower molecular weight of 70,000 was determined by vapor pressure osmometry). The polymers such as the Luviform and Gantrez polymers may be incorporated into the gel dentifrices in solid form or in aqueous solution. When aqueous solution is employed, the aqueous solvent forms a portion of the total water in the liquid vehicle. The mentioned Luviform and Gantrezes are all linear copolymers but cross-linked polymers, such as those sold under the trademark Carbopol, of B.F. Goodrich, e.g., Carbopols 934, 940 and 941, may be substituted, at least in part (e.g., about 1% or more).

Other water-swellable polymeric polycarboxylates include the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylic acid with methyl or hydroxyethyl methacrylate, methyl or ethyl acrylate, isobutyl vinyl ether or N-vinyl-2-pyrrolidone.

Additional water-swellable polymeric polycarboxylates include copolymers of maleic anhydride with styrene, isobutylene or ethyl vinyl ether, polyacrylic, polyitaconic and polymaleic acids, and sulfoacrylic oligomers of M.W. as low as 1,000, available as Uniroyal ND-2.

Suitable, also, generally are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrilacrylic, muconic, itaconic, citraconic, mesaconic, glutaconic, aconitic, alpha-phenylacrylic, 2-benzyl acrylic, 2-cyclohexlacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

The synthetic anionic polymeric polycarboxylate component is mainly a hydrocarbon with optional halogen and O-containing substituents and linkages as present in, for example, ester, ether and OH groups and when present is employed in the instant compositions in approximate weight amounts of 1%–4%, preferably 2%–3%, more preferably 2%–2.5%.

When, as in the present invention, the water-swellable synthetic anionic polymeric polycarboxylate is used in amount of at least 1% by weight, it is very desirable to employ a substantially water-insoluble noncationic antibacterial agent as described in previously mentioned in incorporated British Patent Publications 2235133A, 2227660A, and 2200551A; and U.S. Pat. No. 4,894,220, for antiplaque effectiveness. These include halogenated diphenyl ethers such as triclosan and 2,2'-dihydroxy-5-5'-dibromo-diphenyl ether as well as phenolic compounds including phenol and its homomogs, mono-and poly-alkyl and aromatic halophenols, resorcinol and its derivatives and bisphenolic compounds. Hexyl resorcinol is particularly worthy of mention. Other types include halogenated salicylanilides, benzoic esters and halogenated carbanilides. When present, the antibacterial agent is employed in an effective antiplaque amount, typically about 0.01%–5% by weight, preferably about 0.3%–0.5%.

Optionally linear molecularly dehydrated polyphosphate salt anticalculus agent may also be present in amount of about 0.1%–7% by weight, preferably about 2%–7%. These include wholly or partially neutralized water soluble alkali metal (e.g. potassium or preferably sodium) or ammonium salts such as sodium hexametaphosphate, sodium tripolyphosphate, disodium diacid pyrophosphate, trisodium monoacid pyrophosphate, tetrasodium pyrophosphate and tetrapotassium pyrophosphates as well as mixtures. When both substantially water-insoluble noncationic antibacterial agent and polyphosphate salt are present it is desirable that the weight ratio of polymeric polycarboxylate to polyphosphate be at least about 1.6:1 to about 2.7:1.

Gel dentifrices have their gel consistency provided by a natural or synthetic binder, thickener or gelling agent in p-coportions of about 0.1 to about 10% by weight, preferably about 0.5 to about 5%. A suitable thickener is synthetic hectorite, a synthetic colloidal magnesium alkali metal silicate complex clay available for example as Laponite (e.g. CP, SP 2002, D) marketed by Laporte Industries Limited. Laponite D analysis shows, approximately by weight, 58.00% $SiO_2$, 25.40% Mg), 3.05% $Na_2O$, 0.98% $Li_2O$, and some water and trace metals. Its true specific gravity is 2.53 and it has an apparent bulk density (g./mi. at 8% moisture) of 1.0.

Other suitable thickeners include Irish moss, iota carragenan, gum tragacanth starch, polyvinylpyrrolidone, hydroxyethylpropylcellulose, hydroxybutyl methyl cellulose, hydroxypropyl methyl cellulose, hydroxyethyl cellulose (e.g. available as Natrosoi), sodium carboxymethyl cellulose, and colloidal silica such as finely ground Syloid (e.g. 244). Sodium carboxymethyl cellulose is preferred, even including grades having a viscosity above 20 cps measured as 1% aqueous solution at 25° C., e.g. CMC-7MF and CMC-7MFX available from Hercules.

It will be understood that, as is conventional, the gel dentifrice preparations are to be sold or otherwise distributed in suitably labelled collapsible tubes, typically aluminum, lined lead or opaque or clear plastic, or other squeeze, pump or pressurized dispenser for metering out the contents, having a label describing it in substance, as a gel dentifrice or toothpaste.

Organic surface-active agents are used in the compositions of the present invention to achieve increased prophylactic action, assist in achieving thorough and complete dispersion of the anticalculus agent throughout the oral cavity, and render the instant compositions more cosmetically acceptable. The organic surface-active material is preferably anionic, nonionic or ampholytic in nature, and it is preferred to employ as the surface-active agent a deterslye material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxypropane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarcosinate compounds in the oral compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

Various other materials may be incorporated in the gel dentifrices of this invention such as preservatives, silicones, other anticalculus agents, water-soluble dyes, iridescent particles and/or ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, d-tryptophan, dihydrochalcones, sodium cyclamate, perillartine, APM (aspartyl phenyl alanine, methyl ester), saccharine and the like. Suitably, flavor and sweetening agents may together comprise from about 0.1% to 5% or more of the preparation.

The gel dentifrices may be prepared in accordance with generally employed preparation techniques, with uniform appearance or with stripes.

The following examples are further illustrative of the nature of the present invention, but it is understood that the invention is not limited thereto. All amounts and proportions referred to herein and in the appended claims are by weight unless otherwise indicated.

EXAMPLE 1

The following gel dentifrice is prepared:

|  | Parts | |
|---|---|---|
| Glycerine (99.5% Solution) | 9.950 Glycerine | 0.050 Water |
| Sorbitol (70% Solution) | 33.880 Sorbitol | 14.570 Water |
| Sodium Carboxymethyl Cellulose - 7MF | 0.400 | |
| Iota Carrageenan | 0.400 | |
| Sodium Fluoride | 0.243 | |
| Sodium Saccharin | 0.300 | |
| Polyvinylmethyl Ether/Maleic anhydride-Gantrez S-97 | 2.000 | |
| Sodium Hydroxide (50% Solution) | 0.600 Sodium Hydroxide | 0.600 Water |
| Precipitated silica-Zeodent 113 | 22.000 | |
| Sodium Lauryl Sulfate | 1.500 | |
| Flavor | 1.000 | |
| Triclosan | 0.300 | |
| Water-deionized | | 12.257 |
| Total water - | | 27.477 Parts |

The gel dentifrice is and remains very transparent.

The refractive index of Zeodent 113 is 1.430. The calculated refractive index of the liquid vehicle components, water, glycerine and 70% sorbitol is 1.437. In spite of the differences in refractive indices, clarity results. A substantial part of water hydrates the swellable Gantrez copolymer.

EXAMPLE 2

The following primary gel dentifrice of this example is prepared:

|  | Parts | |
|---|---|---|
| Glycerine (99.5%) | 9.950 Glycerine | 0.050 Water |
| Sorbitol (70%) | 38.880 Sorbitol | 14.520 Water |
| Sodium Carboxymethyl Cellulose - 7MF | 0.400 | |
| Iota Carrageenan | 0.400 | |
| Sodium Fluoride | 0.243 | |
| Sodium Saccharin | 0.300 | |
| Polyvinylmethyl Ether/Maleic andride-Luviform FA 139 (35%) | 1.842 Luviform | 3.421 Water |
| Sodium Hydroxide (50%) | 0.600 Sodium Hydroxide | 0.600 Water |
| Precipitated silica-Zeodent 113 | 22.000 | |
| Sodium Lauryl Sulfate | 1.500 | |
| Flavor | 1.000 | |
| Triclosan | 0.300 | |
| Water-deionized | | 8.994 |
| Total water - | | 27.585 Parts |

The primary gel dentifrice is highly transparent after stabilizing for about 12 hours at room temperature following preparation and remains so.

A variant gel dentifrice in which the liquid vehicle contents are varied as follows:

|  | Parts | |
|---|---|---|
| Glycerine (99.5%) | 22.686 (Glycerine) | 0.114 Water |
| Sorbitol (70%) | 23.870 (Sorbitol) | 10.23 Water |
| Water-deionized | | 10.50 |
| Total Water (including 0.600 parts from 50% solution of sodium hydroxide and 3.421 (parts from 35% solution of Luviform) = | | 24.865 |

The variant gel dentifrice is and remains turbid and very cloudy.

The refractive index of Zeodent 113 is 1.430. The calculated refractive index of the primary gel dentifrice is 1.4378 while the calculated refractive index of the variant gel dentifrice, containing less water, is 1.4373. Even though the refractive index of the varient gel is somewhat closer to the refractive of Zeodent 113, nevertheless, the primary gel dentifrice possesses much superior clarity.

EXAMPLE 3

The following very clear gel dentifrice is prepared:

|  | Parts | |
|---|---|---|
| Sorbitol (70%) | 41.800 Sorbitol | 17.920 Water |
| Sodium Carboxymethyl Cellulose - 7MF | 0.400 | |
| Iota Carrageenan | 0.400 | |
| Sodium Fluoride | 0.243 | |
| Sodium Saccharin | 0.300 | |
| Polyvinylmethyl Ether/Maleic Anhydride-Luviform FA 139 (35%) | 1.842 Luviform | 3.421 Water |
| Sodium Hydroxide (50%) | 0.600 Sodium Hydroxide | 0.600 Water |
| Precipitated silica-Zeodent 113 | 22.000 | |
| Sodium Lauryl Sulfate | 1.500 | |
| Flavor | 1.000 | |
| Triclosan | 0.300 | |
| Water-deionized | | 7.674 |
| Total water - | | 29.615 Parts |

This invention has been described with respect to certain preferred embodiments and it will be understood that modifications and variations thereof obvious to those skilled in the art are to be included within the purview of this application and the scope of the appended claims.

We claim:

1. A visually clear gel dentifrice comprising about 5-50% by weight of a dentally acceptable dentifrice polishing agent having a refractive index in the range of about 1.41 to about 1.47, an effective antiplaque amount of a substantially water-insoluble non-cationic antibacterial agent, about 0.1%-10% by weight of a gelling agent to provide a gel consistency to said dentifrice, a liquid vehicle comprising an amount of at least 25% up to 30% by weight of said dentifrice of total water and about 30%-45% by weight of said dentifrice on a net basis of sorbitol humectant material wherein sorbitol is present as the main or only humectant component in neat amount of at least about 30% by weight of said dentifrice and other humectant, if present, is in neat amount up to 15% by weight and about 1%–4% neat amount by weight of dentifrice of a water-swellable synthetic anionic polycarboxylate polymer, wherein the visual clarity of said gel dentifrice is and remains stable.

2. The visually clear dentifrice claimed in claim 1 wherein said polishing agent is present in amount of about 10%–30% by weight.

3. The visually clear dentifrice claimed in claim 2 wherein said polishing agent is a siliceous polishing agent.

4. The visually clear dentifrice claimed in claim 3 wherein said siliceous polishing agent is a precipitated silica.

5. The visually clear gel dentifrice claimed in claim 4 wherein said precipitated silica polishing agent is present in amount of about 15%–25% by weight.

6. The visually clear gel dentifrice claimed in claim 1 wherein said liquid vehicle comprises up to about 15% by weight of an additional humectant material.

7. The visually clear gel dentifric claimed in claim 1 wherein said antibacterial agent is triclosan and is present in amount of about 0.01%–5% by weight.

8. The visually clear gel dentifrice claimed in claim 7 wherein said triclosan is present in amount of about 0.3%–0.5% by weight.

9. The visually clear gel dentifrice claimed in claim 8 wherein said liquid vehicle comprises up to about 15% by weight of an additional liquid humectant material which is at least one of glycerine, propylene glycol and polypropylene glycol.

10. The visually clear gel dentifrice claimed in claim 9 wherein said additional humectant material comprises about 3%–10% by weight of glycerine.

11. The visually clear gel dentifrice claimed in claim 1 wherein about 0.1%–7% by weight of a linear molecularly dehydrated polyphosphate salt anticalculus agent is also present.

12. The visually clear gel dentifrice claimed in claim 1 wherein about 0.1%–7% by weight of a linear molecularly dehydrated polyphosphate salt anticalculus agent is also present.

13. The visually clear gel dentifrice claimed in claim 1 wherein said polycarboxylate polymer is present in amount of about 2%–3% by weight.

14. The visually clear gel dentifrice claimed in claim 1 wherein said polycarboxylate polisher is polyvinyl methyl ether/maleic anhydride copolymer.

* * * * *

UNITED STATES PATENT AND TRADEMARK OFFICE
CERTIFICATE OF CORRECTION

PATENT NO. : 5,354,550

DATED : October 11, 1994

INVENTOR(S) : Michael Alan Collins and Joan Marie Duckenfield

It is certified that error appears in the above-indentified patent and that said Letters Patent is hereby corrected as shown below:

On title page, item [75], the following should be added:
—Benjamin Y. Mandanas, Freehold, N.J.—

Column 7, Line 17, cancel "14.570" and insert --14.520--.

Column 7, line 52, cancel "38.880" and insert --33.880--.

Signed and Sealed this

Eighth Day of October, 1996

Attest:

BRUCE LEHMAN

Attesting Officer

Commissioner of Patents and Trademarks